United States Patent
Linares

(10) Patent No.: US 10,022,237 B2
(45) Date of Patent: Jul. 17, 2018

(54) MULTI-COMPONENT IMPLANT ASSEMBLY WITH DUAL ARTICULATING AND/OR ROTATING SURFACES

(71) Applicant: Linares Medical Devices, LLC, Auburn Hills, MI (US)

(72) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 0 days.

(21) Appl. No.: 15/459,759

(22) Filed: Mar. 15, 2017

(65) Prior Publication Data

US 2017/0181859 A1    Jun. 29, 2017

Related U.S. Application Data

(60) Division of application No. 14/803,696, filed on Jul. 20, 2015, now abandoned, which is a (Continued)

(51) Int. Cl.
*A61F 2/40* (2006.01)
*A61F 2/30* (2006.01)

(52) U.S. Cl.
CPC .......... *A61F 2/4003* (2013.01); *A61F 2/4014* (2013.01); *A61F 2/4081* (2013.01); *A61F 2002/305* (2013.01); *A61F 2002/30364* (2013.01); *A61F 2002/30484* (2013.01); *A61F 2002/30507* (2013.01);
(Continued)

(58) Field of Classification Search
CPC .................. A61F 2/4081; A61F 2/4014; A61F 2002/30332; A61F 2/40; A61F 2/4059; A61F 2002/30604; A61F 2002/4085; A61F 2220/0025; A61F 2/4612
See application file for complete search history.

(56) References Cited

U.S. PATENT DOCUMENTS

| 1,051,444 A | 1/1913 | Pleister |
| 2,314,445 A | 3/1943 | DuVall |
(Continued)

FOREIGN PATENT DOCUMENTS

| EP | 1228739 A2 | 8/2002 |
| WO | 199800076 A1 | 1/1998 |
(Continued)

OTHER PUBLICATIONS

Tan et al., "Developments of an Antimicrobial Microporous Polyurethane Membrane", Journal of Membrane Science, 289. 199-209 (2007).

*Primary Examiner* — Ann Schillinger
(74) *Attorney, Agent, or Firm* — Dinsmore & Shohl LLP

(57) ABSTRACT

An implant assembly for re-establishing a glenohumeral joint between a scapula and humerus. A first receiver is adapted to being mounted to a reconditioned glenoid cavity defined in the scapula, with a second receiver adapted to being mounted to a reconditioned humeral head associated with the humerus. A three dimensional and at least partially spherical shaped component is interposed between the first and second receivers for establishing each of a first articulating surface with the first receiver and a rotating interface with the second receiver.

4 Claims, 14 Drawing Sheets

Related U.S. Application Data continuation-in-part of application No. 13/592,687, filed on Aug. 23, 2012, now abandoned.

(60) Provisional application No. 61/526,388, filed on Aug. 23, 2011, provisional application No. 61/526,404, filed on Aug. 23, 2011.

(52) U.S. Cl.
CPC ............ *A61F 2002/30642* (2013.01); *A61F 2002/30649* (2013.01); *A61F 2002/30878* (2013.01); *A61F 2002/4022* (2013.01)

(56) References Cited

U.S. PATENT DOCUMENTS

| | | |
|---|---|---|
| 2,667,644 A | 2/1954 | Johnson |
| 2,821,979 A | 2/1958 | Cameron |
| 3,694,820 A | 10/1972 | Scales et al. |
| 3,815,157 A | 6/1974 | Skorecki et al. |
| 3,916,451 A * | 11/1975 | Buechel ............ A61F 2/32 403/56 |
| 3,918,451 A | 11/1975 | Steil |
| 3,973,277 A | 8/1976 | Semple et al. |
| 4,003,095 A | 1/1977 | Gristina |
| 4,040,131 A | 8/1977 | Gristina |
| 4,045,825 A | 9/1977 | Stroot |
| 4,101,985 A | 7/1978 | Baumann et al. |
| 4,206,517 A | 6/1980 | Pappas et al. |
| 4,483,023 A | 11/1984 | Hoffman, Jr. et al. |
| 4,501,031 A | 2/1985 | McDaniel et al. |
| 4,665,951 A | 5/1987 | Ellis et al. |
| 4,693,723 A | 9/1987 | Gabard |
| 4,744,793 A | 5/1988 | Parr et al. |
| 4,778,473 A | 10/1988 | Matthews et al. |
| 4,792,336 A | 12/1988 | Hlavacek et al. |
| 4,828,562 A | 5/1989 | Kenna |
| 4,840,630 A | 6/1989 | Kitamura |
| 4,851,005 A | 7/1989 | Hunt et al. |
| 4,883,486 A | 11/1989 | Kapadia et al. |
| 4,906,149 A | 3/1990 | Rockenfeller et al. |
| 5,004,474 A | 4/1991 | Fronk et al. |
| 5,078,745 A | 1/1992 | Rhenter et al. |
| 5,171,325 A | 12/1992 | Aulie |
| 5,263,984 A | 11/1993 | Li et al. |
| 5,282,867 A | 2/1994 | Mikhail |
| 5,376,119 A | 12/1994 | Zimmermann et al. |
| 5,389,107 A | 2/1995 | Nassar et al. |
| 5,417,693 A | 5/1995 | Sowden et al. |
| 5,462,563 A | 10/1995 | Shearer et al. |
| 5,486,197 A | 1/1996 | Le et al. |
| 5,507,819 A | 4/1996 | Wolf |
| 5,554,194 A | 9/1996 | Sanders |
| 5,571,191 A | 11/1996 | Fitz |
| 5,575,819 A | 11/1996 | Amis et al. |
| 5,593,448 A | 1/1997 | Dong |
| 5,609,647 A | 3/1997 | K alberer et al. |
| 5,676,702 A | 10/1997 | Ratron et al. |
| 5,702,469 A | 12/1997 | Whipple et al. |
| 5,702,486 A | 12/1997 | Craig et al. |
| 5,707,395 A | 1/1998 | Li |
| 5,723,018 A | 3/1998 | Cyprien et al. |
| 5,728,175 A | 3/1998 | Rincoe |
| 5,741,335 A | 4/1998 | Gerber et al. |
| 5,800,566 A | 9/1998 | Gramnas et al. |
| 5,879,404 A | 3/1999 | Bateman et al. |
| 5,921,358 A | 7/1999 | Gramnas et al. |
| 5,961,555 A | 10/1999 | Huebner |
| 6,001,106 A | 12/1999 | Ryan et al. |
| 6,010,535 A | 1/2000 | Shah |
| 6,190,411 B1 | 2/2001 | Lo et al. |
| 6,193,758 B1 | 2/2001 | Huebner |
| 6,197,063 B1 | 3/2001 | Dews |
| 6,245,109 B1 | 6/2001 | Mendes et al. |
| 6,325,804 B1 | 12/2001 | Wenstrom, Jr. et al. |
| 6,383,223 B1 | 5/2002 | Baehler et al. |
| 6,582,715 B1 | 6/2003 | Barry et al. |
| 6,620,197 B2 | 9/2003 | Maroney et al. |
| 6,626,942 B1 | 9/2003 | Edberg et al. |
| 6,645,251 B2 | 11/2003 | Salehi et al. |
| 6,776,799 B2 | 8/2004 | Ball et al. |
| 6,790,234 B1 | 9/2004 | Frankle |
| 6,818,019 B2 * | 11/2004 | Horber ............ A61F 2/4014 403/90 |
| 6,840,962 B1 | 1/2005 | Vacanti et al. |
| 6,939,379 B2 | 9/2005 | Sklar |
| 6,942,699 B2 | 9/2005 | Stone et al. |
| 6,986,790 B2 | 1/2006 | Ball et al. |
| 7,033,396 B2 | 4/2006 | Tornier |
| 7,044,983 B1 | 5/2006 | Cheng et al. |
| 7,056,340 B2 | 6/2006 | McKernan et al. |
| 7,066,958 B2 | 6/2006 | Ferree |
| 7,077,867 B1 | 7/2006 | Pope et al. |
| 7,087,091 B1 | 8/2006 | Chen et al. |
| 7,097,663 B1 | 8/2006 | Nicol et al. |
| 7,101,398 B2 | 9/2006 | Dooris et al. |
| 7,153,327 B1 | 12/2006 | Metzger |
| 7,169,184 B2 | 1/2007 | Dalla Pria |
| 7,175,663 B1 | 2/2007 | Stone |
| 7,175,666 B2 | 2/2007 | Yao |
| 7,189,261 B2 | 3/2007 | Dews |
| 7,309,360 B2 | 12/2007 | Tornier et al. |
| 7,329,281 B2 | 2/2008 | Hays et al. |
| 7,331,995 B2 | 2/2008 | Eisermann et al. |
| 7,445,638 B2 | 11/2008 | Beguin et al. |
| 7,462,197 B2 | 12/2008 | Tornier et al. |
| 7,465,319 B2 | 12/2008 | Tornier |
| 7,510,558 B2 | 3/2009 | Tallarida et al. |
| 7,708,781 B2 * | 5/2010 | Scheker ............ A61F 2/3804 623/20.11 |
| 2001/0051831 A1 | 12/2001 | Subba Rao et al. |
| 2002/0013627 A1 | 1/2002 | Geistlich et al. |
| 2002/0143402 A1 | 10/2002 | Steinberg |
| 2003/0130741 A1 | 7/2003 | McMinn |
| 2004/0024460 A1 | 2/2004 | Ferree |
| 2004/0039449 A1 | 2/2004 | Tornier |
| 2004/0064187 A1 | 4/2004 | Ball et al. |
| 2004/0064188 A1 | 4/2004 | Ball et al. |
| 2004/0210317 A1 | 10/2004 | Maroney et al. |
| 2004/0225370 A1 | 11/2004 | Cruchet et al. |
| 2004/0267370 A1 | 12/2004 | Ondrla |
| 2005/0081867 A1 | 4/2005 | Murphy |
| 2005/0107882 A1 | 5/2005 | Stone et al. |
| 2005/0187620 A1 | 8/2005 | Pai et al. |
| 2005/0192674 A1 | 9/2005 | Ferree |
| 2005/0261775 A1 | 11/2005 | Baum et al. |
| 2005/0278032 A1 | 12/2005 | Tornier et al. |
| 2006/0009852 A1 | 1/2006 | Winslow et al. |
| 2006/0020344 A1 | 1/2006 | Shultz et al. |
| 2006/0058886 A1 | 3/2006 | Wozencroft |
| 2006/0074423 A1 | 4/2006 | Alleyne et al. |
| 2006/0111787 A1 | 5/2006 | Bailie et al. |
| 2006/0149370 A1 | 7/2006 | Schmieding et al. |
| 2007/0005074 A1 | 1/2007 | Chudik |
| 2007/0005137 A1 | 1/2007 | Kwak |
| 2007/0088442 A1 | 4/2007 | Cima et al. |
| 2007/0179624 A1 | 8/2007 | Stone et al. |
| 2008/0234830 A1 | 9/2008 | Hershberger et al. |
| 2009/0039164 A1 | 2/2009 | Herwig et al. |
| 2009/0088865 A1 | 4/2009 | Brehm |
| 2009/0287309 A1 | 11/2009 | Walch et al. |
| 2009/0292364 A1 | 11/2009 | Linares |
| 2010/0049327 A1 | 2/2010 | Isch et al. |
| 2011/0098822 A1 | 4/2011 | Walch et al. |

FOREIGN PATENT DOCUMENTS

| | | |
|---|---|---|
| WO | 1998000076 A1 | 1/1998 |
| WO | 2004080331 A2 | 9/2004 |
| WO | 2009039164 A1 | 3/2009 |

* cited by examiner

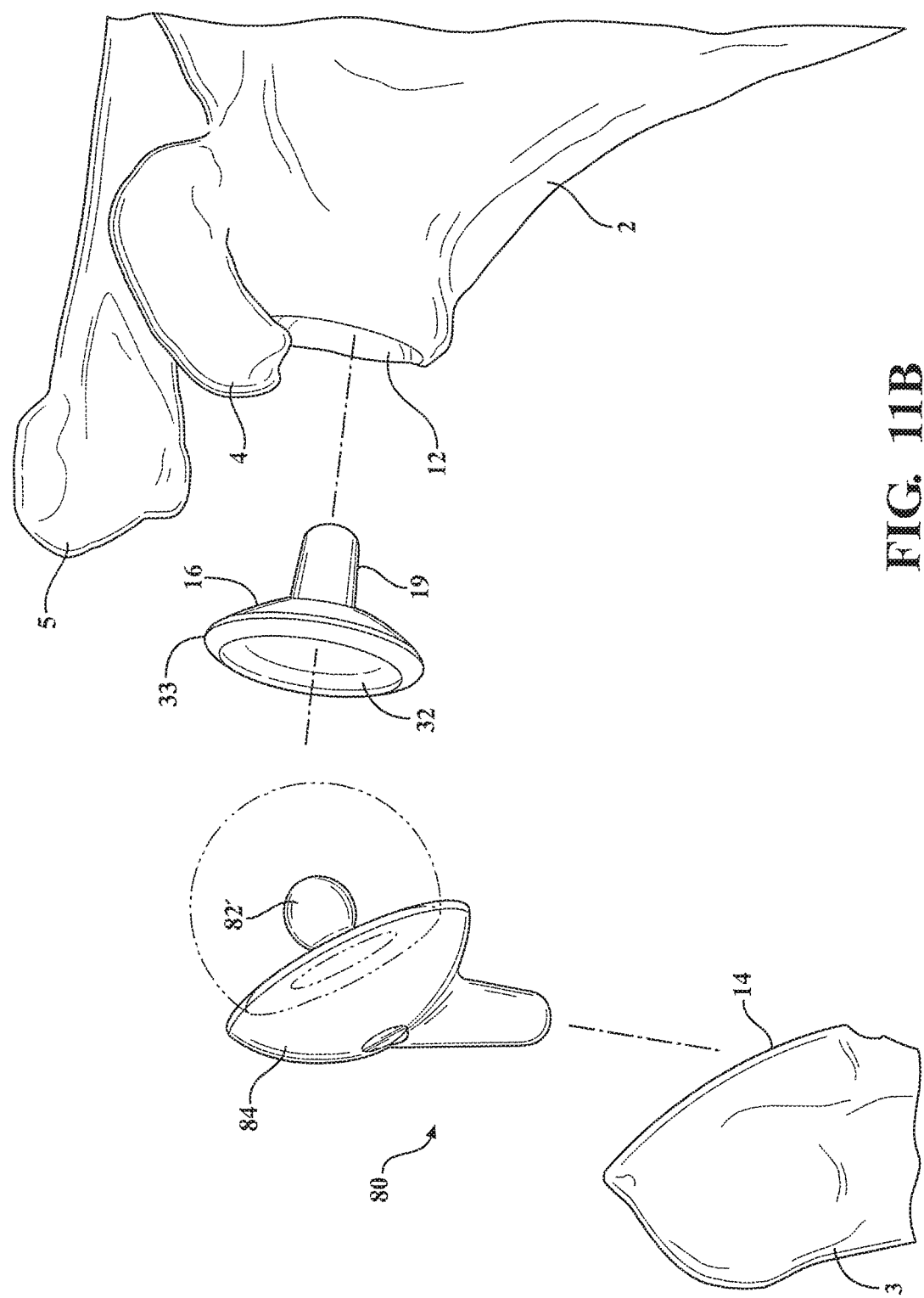

MULTI-COMPONENT IMPLANT ASSEMBLY WITH DUAL ARTICULATING AND/OR ROTATING SURFACES

CROSS REFERENCE TO RELATED APPLICATIONS

This Application is a Divisional of application Ser. No. 14/803,696 filed Jul. 20, 2015. Application Ser. No. 14/803,696 is a Continuation-in-part of application Ser. No. 13/592,687 filed on Aug. 23, 2012. Application Ser. No. 13/592,687 claims the benefit of U.S. Provisional Application 61/526,388 fled on Aug. 23, 2011. Application Ser. No. 13/592,687 claims the benefit of U.S. Provisional Application 61/526,404 filed on Aug. 23, 2011, the contents of which are incorporated herein in their entirety.

BACKGROUND OF THE INVENTION

Field of the Invention

The present invention is directed to a shoulder implant assembly and, more specifically, to a multi-component implant assembly including a pair of receivers mounted to first and second shoulder joint defining bones. An intermediated positioned and pseudo-spherical (defined as substantially spherical with a flattened base) shaped intermediate component engages a first of the bone mounted receivers in an articulating relationship and further engages a second of the bone mounted receivers in a rotation relationship, thereby providing evenly distributed wear profiles for increased useful life of the implant, as well as relieving associated ligament tension.

Description of the Background Art

The prior art discloses various types of artificial implants, such as replacing damaged natural joint constructions including those for the shoulder. Examples of these include each of the modular humeral head resurfacing system of Winslow et al., US 2006/0009852 and US 2005/0107882, each of which incorporates a two piece humeral component for use in joint arthroplasty which is adapted to be implanted into a joint and engaged by a likewise implanted socket component.

U.S. Pat. No. 6,942,699, to Stone et al., teaches a modular shoulder prosthesis having an adjustable radial offset and/or angular inclination provided by relative rotation of an adapter interdisposed between a stem and a head. Specifically, the interface configuration between the stem and the adapter, as well as between the adapter and the head are designed such that relative positioning of these components provides a continuous adjustment in the radial offset and/or angular inclination. Indicia are provided at the interface between the adapter and the head to precisely determine the magnitude and direction of the adjustment being made.

U.S. Pat. No. 6,818,019, to Horber, teaches a joint prosthesis with a head cap connected via a collar piece to a shaft piece which may be anchored in the bone. The collar piece is coupled to the shaft piece by a joint head in a ball-jointed manner. The articulation surfaces between the joint cavity in the shaft piece and the articulation head on the collar piece are embodied such that on pressing the articulation head to the base of the joint cavity, edges or projections on the one articulation surface digs into the other articulation surface lying on a virtual spherical surface. A ball-joint like articulation is provided, whereby the spherical surfaces may have a relatively large production tolerance without the above affecting the clamping connection between the articulation surfaces.

Finally, U.S. Pat. No. 3,916,451 to Buechel et al. teaches prosthetic joints of the type used to replace dysfunctional natural joints such as the shoulder, hip, and knee. Provision of an intermediate floating bearing element to which are rotatably engaged members which are in turn secured to the appropriate bone structures results in enhanced relative motion and improved resistance to dislocation. A flange or "skirt" on the floating bearing element provides additional strength and improved function. The invention is suited to embodiments in both ball and socket and hinge type joints. Assembly and disassembly of the joint are facilitated by two-piece construction of the floating bearing element and the use of snap rings for attaching fixed bearing elements to components which may be permanently secured to the bone structure. The snap rings may be designed to support normal loads yet fracture without damage to the other components, where necessary to disassemble an implanted prosthetic joint.

SUMMARY OF THE PRESENT INVENTION

The present invention discloses an implant assembly for re-establishing a glenohumeral joint between a scapula and humerus. A first receiver is adapted to being mounted to a reconditioned glenoid cavity defined in the scapula, with a second receiver adapted to being mounted to a reconditioned humeral head associated with the humerus. A three dimensional and at least partially spherical shaped component (pseudo spherical component) with a flattened end is interposed between the first and second receivers for establishing each of articulating and rotating support at respective and spaced apart seating profiles established with the first and second receivers.

Additional features include the first receiver exhibiting a first concave profile seating a spherical portion of the interposed three dimensional (pseudo spherical) component for establishing a first universal articulating interface. In a first embodiment, a bulbous projection extends from a planar annular profile associated with the second humeral head mounted receiver. The bulbous portion resistively fits within an opposing and mating undercut profile defined in a flattened end profile of the pseudo-spherical component for establishing a second rotational interface.

A slot or passageway communicates from a rear convex surface of the secondary receiver in extending fashion into the bulbous projection, such that the bulbous projection can exhibit a split or otherwise expandable construction. Upon pre-engaging the bulbous projection into the undercut surface communicable portion of the partially spherical shaped element, a pin or other fastener is inserted through the rear surface of the secondary receiver in order to expand the expand the bulbous portion into a more secure engagement with the partially spherical shaped element and while still allowing for inter-rotational support at the interface established between the second receiver and intermediate component.

In a second embodiment the second receiver is reconfigured as first and second mating and linearly split halves. Each of the halves exhibits an undercut or other inner expanding configuration in communication with its flattened end profile. Prior to mounting (e.g. by gluing) to the reconditioned humeral head, the mating halves are pre-assembled (snappingly engaged together) so as to capture therebetween a mating portion associated with a reconfigured pseudo-spherical and intermediate component, the mating portion projecting from e flattened end profile of the intermediate component.

Other features include the first receiver exhibiting a tapered rim extending around an outer perimeter of its concave profile for establishing enhanced shouldering support of the spherical portion. Each of the first and second receiver components and interposed pseudo-spherical component may also be constructed of an alternating material including at least one of a polymer, polymer composite, metal, metal composite or polymer/metal admixture.

BRIEF DESCRIPTION OF THE DRAWINGS

Reference will now be made to the attached drawings, when read in combination with the following detailed description, wherein like reference numerals refer to like parts throughout the several views, and in which:

FIGS. 11A and 11B illustrate another variant similar in most respects to FIGS. 10A-10B, the bulbous portion being reconfigured without a split profile while expanding upon rear insertion of the pin;

DETAILED DESCRIPTION OF THE PREFERRED EMBODIMENTS

As will be described in additional detail with reference to the succeeding variants, the present invention discloses a multi-component shoulder implant assembly for providing an in-situ and reconditioned installation option which is an improvement over other conventional joint implant installations.

Figure 5:
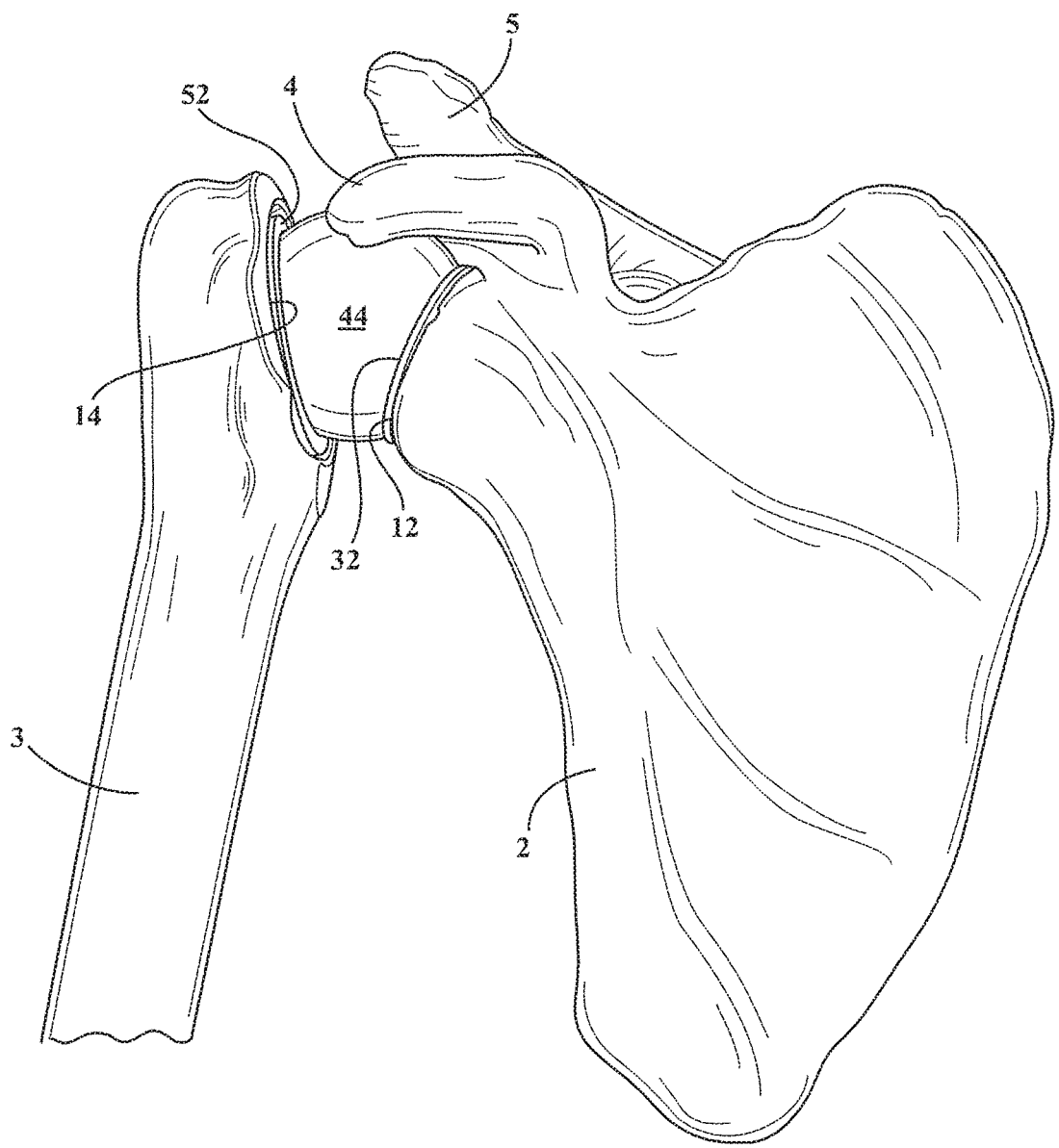
FIG. 5 is an assembled view of a yet further modified shoulder implant assembly.
Figure 6:
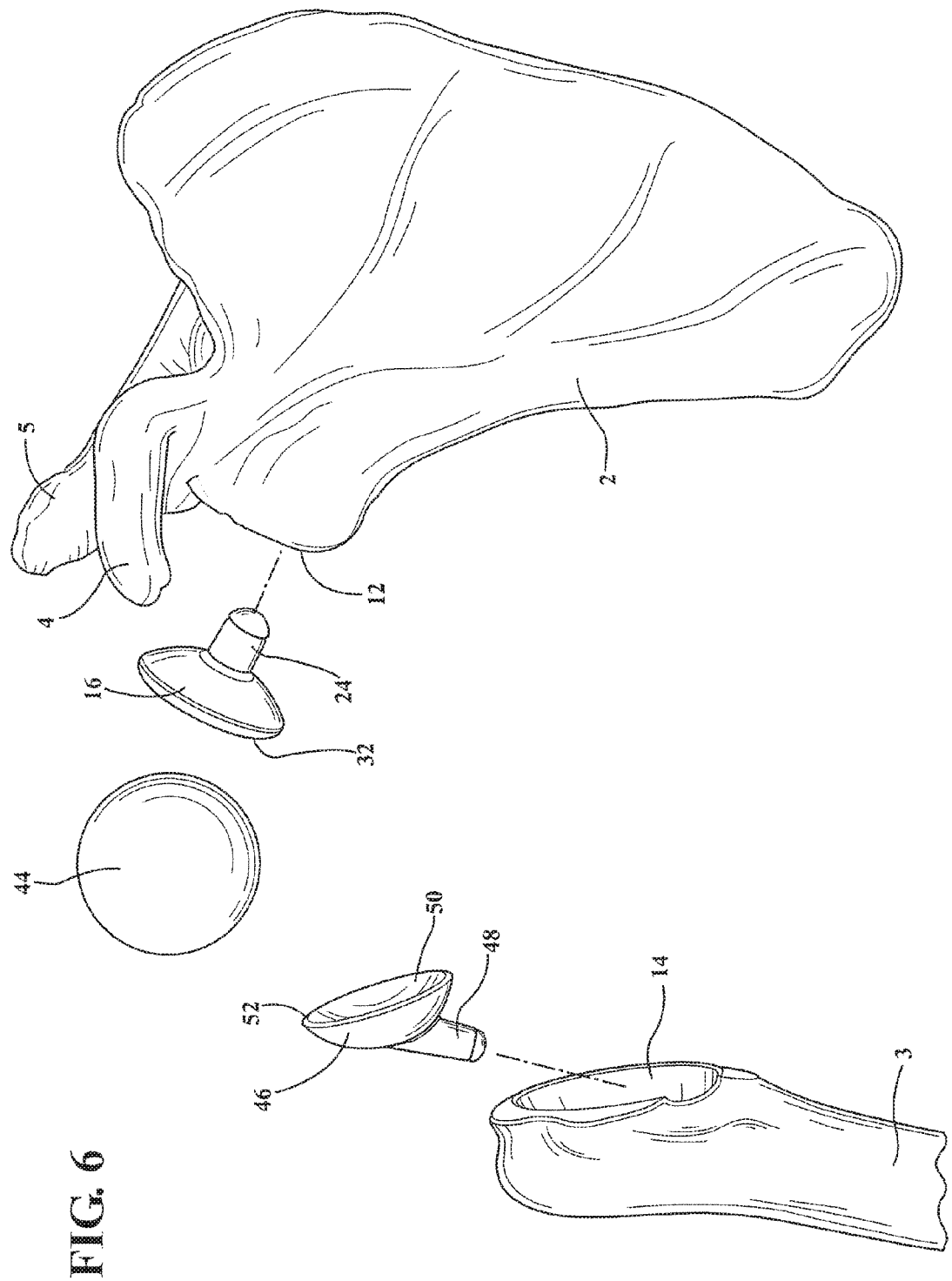
FIG. 6 is an exploded view of the arrangement of FIG. 5 and better depicting the arrangement of a scapula mounted first receiver such as depicted in FIGS. 1-2, combined with a second receiver configured as shown in FIGS. 3-4, and in combination with a fully spherical shaped intermediate component for providing universal articulating support along each of two individual locations established between the humerus mounting receiver and intermediate component, and separately an opposite end profile of the intermediate component and the other receiver mounted in the scapula.
Figure 7:
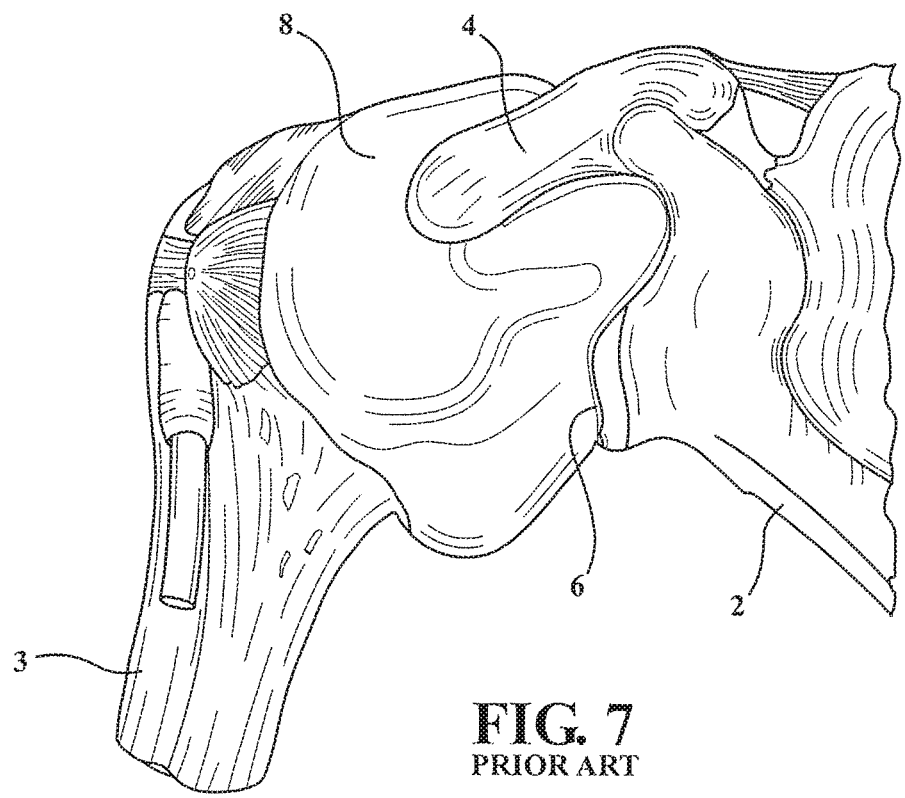
FIGS. 7-9 depict a series of supporting Prior Art illustrations of a human anatomical shoulder joint, and for which the multi-component assembly provides an in situ and reconditioned implantation option.
Figure 9:
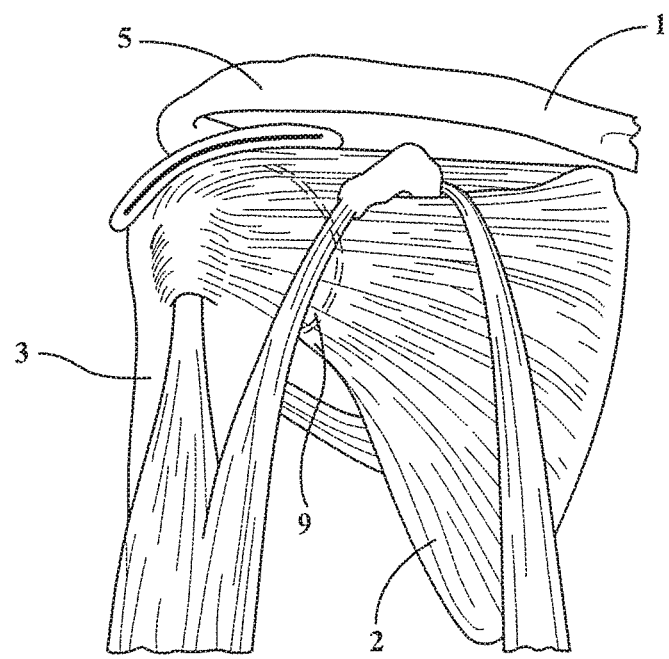
Figure 8:
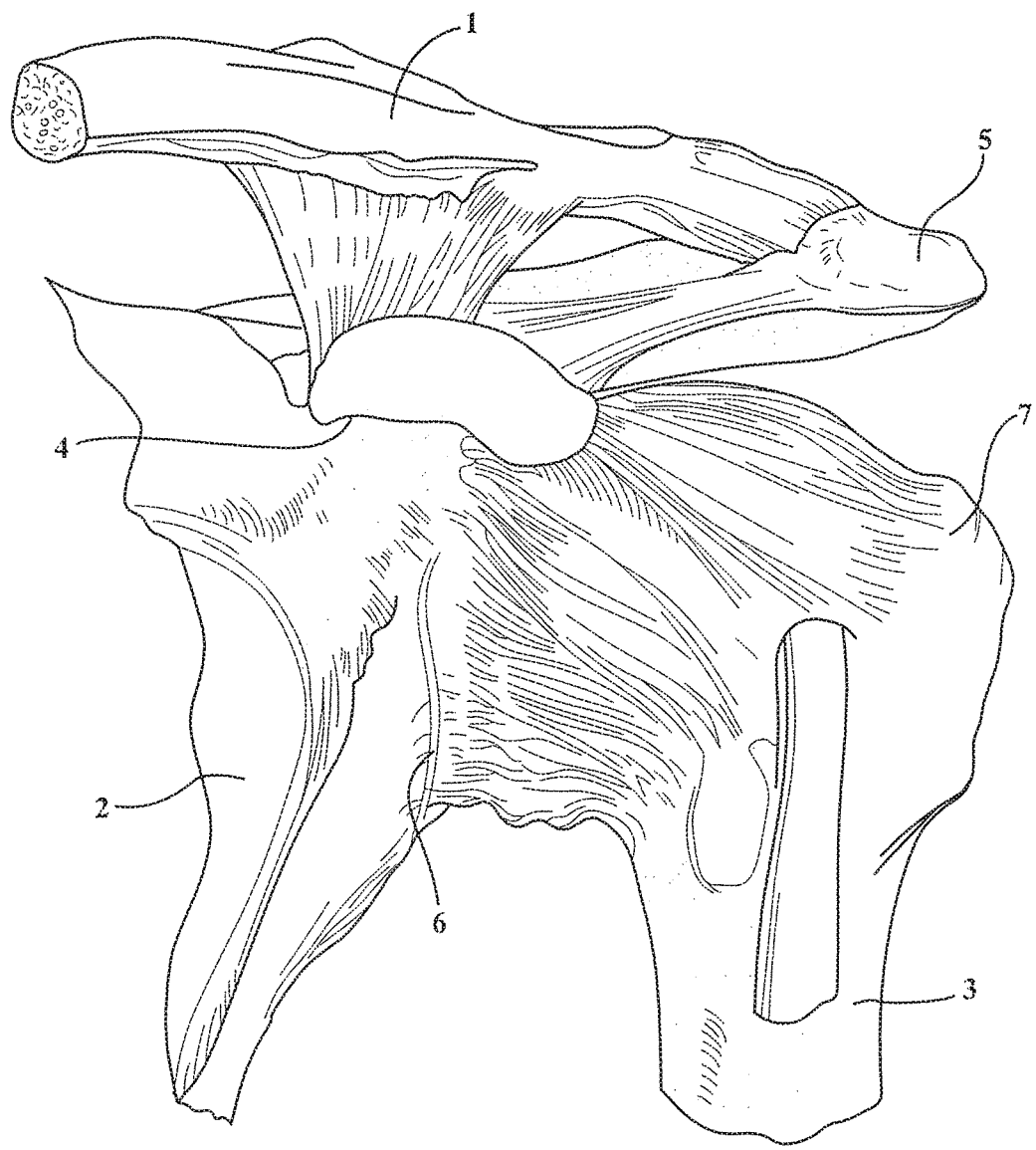

Prior to describing in detail the configurations of the various embodiments of multi-component shoulder implants, respectively depicted in FIGS. 1-2, 3-4, 5-6, 10A-10B, 11A-11B, 12 and 13, a Prior Art depiction of an anatomically correct human shoulder is shown in FIGS. 7-9 and which includes three bones consisting of the clavicle (collarbone) 1, the scapula (shoulder blade) 2, and the humerus (upper arm bone) 3, as well as associated muscles, ligaments and tendons (see in particular FIGS. 8 and 9). The articulations between the bones of the shoulder collectively make up the shoulder joints where the humerus 3 attaches to the scapula 2.

An abbreviated and incomplete description of the scapula further includes, at strategic locations a coracoid process 4 and spine connected acromion 5, in the proximity of which is configured the glenoid cavity 6. The humerus 3 terminates, in relevant part, at an upper end located humeral head 7 (FIG. 8) which generally seats via an interposed bursa 8 (FIG. 7).

The three joints of the shoulder further include each of the glenohumeral, acromioclavicular and sternoclavicular joints. The glenohumeral joint, see as identified at 9 in FIG. 9, is the main joint of the shoulder and the generic term "shoulder joint" usually refers to this ball and socket joint that allows the arm to rotate in a circular fashion or to hinge out and up away from the body.

As is best depicted in the prior art view of FIG. 8, associated types of joint cartilage include articular cartilage located on the ends of the bones and which allows the bones to glide and move on each other and labrum cartilage located in the shoulder. In combination, the shoulder as constructed exhibits sufficient mobile for undertaking a wide range of actions of the arms and hands as well as being sufficiently stable as to allow for actions such as lifting, pushing and pulling. This compromise between mobility and stability results in a large number of shoulder problems not faced by other joints such as the hip.

With reference now to the embodiments of the invention, and for purposes of ease and clarity of illustration, a simplified depiction is shown of the glenohumeral joint established between the scapula 2 and humerus 3 and in which all ligaments, muscles and tendons are removed. In each instance, and prior to installation of the multi-component implant assembly (such as occurring after significant degradation of the natural glenohumeral joint or in other instances in which an accident or other traumatic incident has resulted in significant damage), an initial (in situ) surgical reconditioning procedure is employed of the opposing joint defining surfaces established by the humeral head 7 and the glenoid cavity 6. This includes employing relevant surgical drilling and shaping instruments (also not shown) in order to prepare the joint defining locations of the bones for subsequently attaching selected components associated with the implant assembly and as will now be described.

Figure 1:
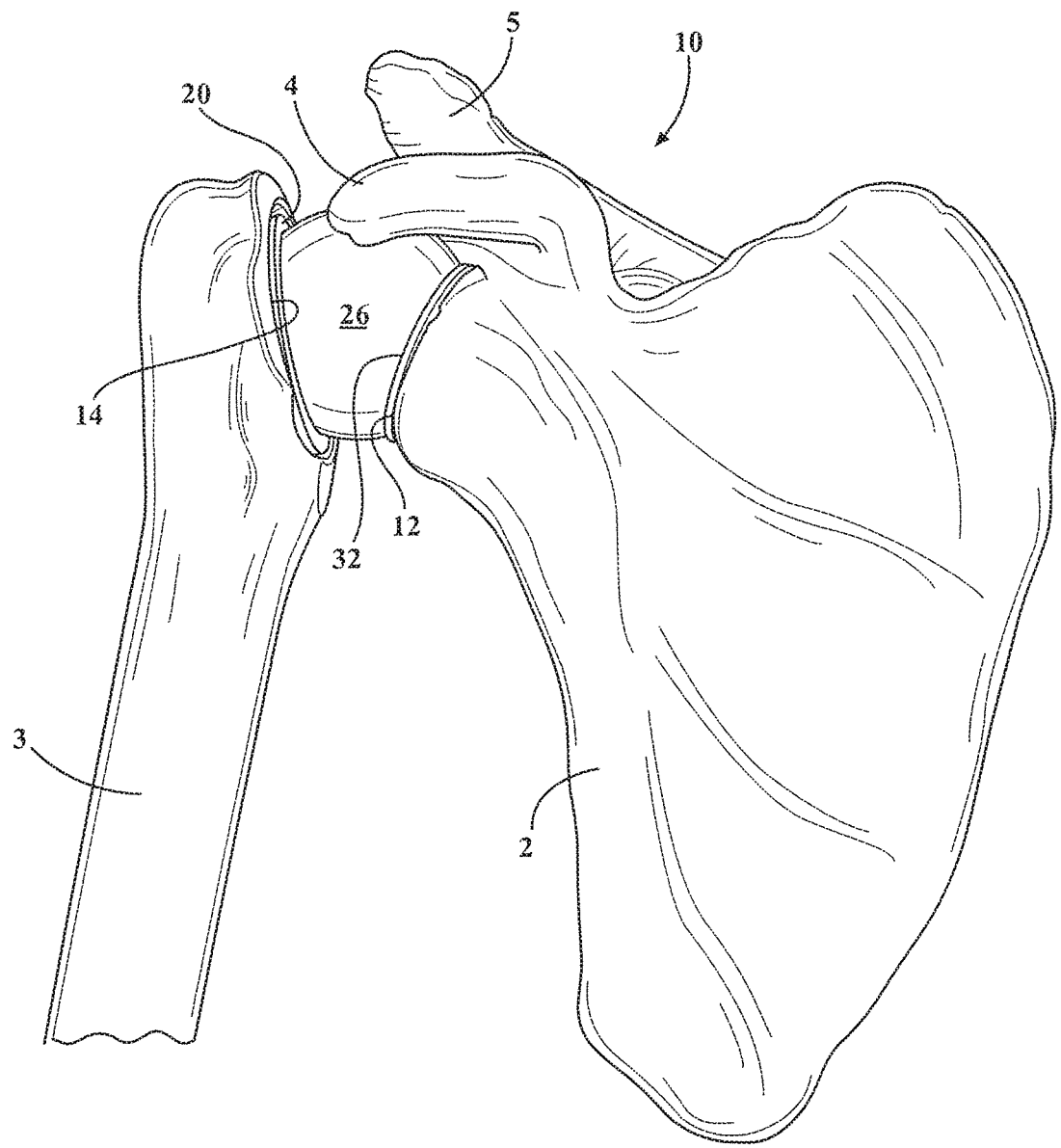
FIG. 1 is an assembled view of a first shoulder implant assembly.
Figure 2:
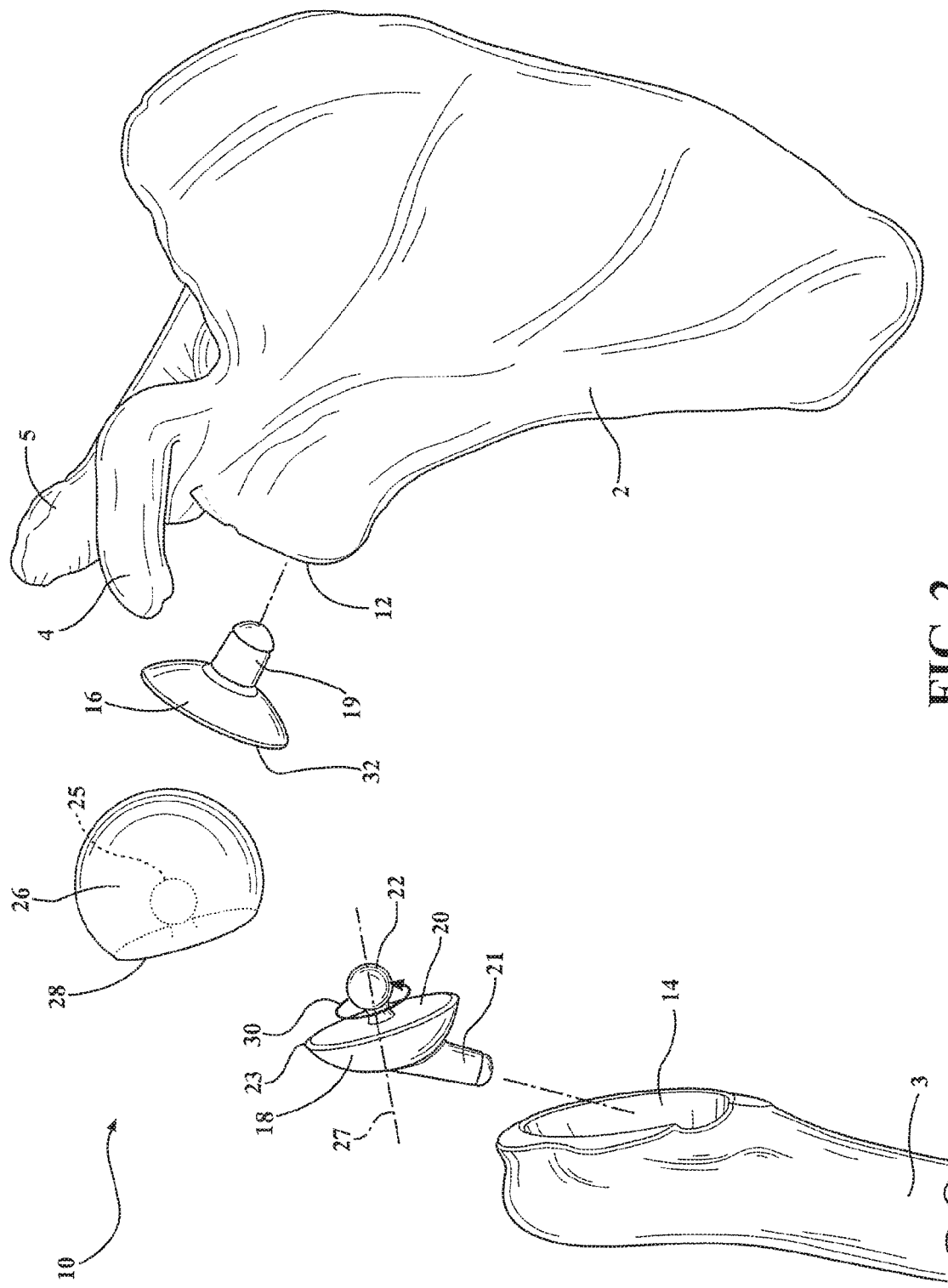
FIG. 2 is an exploded view of the multi-component implant arrangement of FIG. 1 for reconditioned re-engagement of a patient's scapula and upper humerus bones and better depicting the respective mounted first and second uniquely configured receiver components, along with an intermediate and universally inter-supported and substantially spherical shaped component exhibiting a flattened profile opposing the humeral head mounted receiver with projecting bulb seating portion and in order to provide rotating support in combination with universal articulating support separately established between the intermediate component and the opposite scapula bone mounted receiver.

The above stated, and referring initially to each of FIGS. 1 and 2, a pair of assembled and exploded views, both generally at 10, are depicted of a first variant of shoulder implant assembly for installation within reconditioned and opposing end locations of the patient's scapula 2 (represented by reconditioned profile 12) and humerus (further represented by reconditioned profile 14), and as is best shown in the exploded view of FIG. 2. The implant assembly 10 includes, collectively, a first receiver shaped component 16 which is mounted within the reconditioned recess 12 of the scapula glenoid cavity.

A secondary and pseudo-receiver shaped component 18 likewise mounted within the reconditioned recess 14 of the upper humeral head. The secondary receiver 18 exhibits a planar and generally annular shaped surface profile 20 from which generally centrally projects a bulbous portion 22 which is interconnected to the planar surface profile 20 via a narrowed neck 23.

Each of the first receiver 16 and second receiver 18 further includes a uniquely configured stem portion, see at 19 and 21, respectively, which seats within hidden configured recess configurations (not shown) established within the reconditioned innermost profile 12 of the scapula glenoid cavity and within the corresponding humeral head reconditioned profile 14. In a typical surgical procedure, a medical bonding cement or other suitable fastener/adhesive (not shown) is employed for anchoring the receivers 16 and 18 to the respective bone locations 2 and 3, it being further understood that the configuration of these elements is capable of being reversed (e.g. so that the receiver 16 is mounted to the humeral head and the receiver 18 reversed to mount to the scapula glenoid cavity).

An intermediate and universally inter-supported and substantially (also termed pseudo or partial) spherical shaped element or component is depicted at 26. The intermediate component exhibits a flattened profile 28 opposing the humeral head mounted receiver 18 with its projecting bulb seating portion 22.

Assembling of the secondary receiver 18 with the partially spherical shaped element 26 results in its planar annular profile 20 abutting the flattened profile 28 of the intermediate element, along with the bulbous portion 22 of the secondary receiver resistively engaging a mating and enlarged undercut profile (see in phantom at 25) firmed within the partially spherical shaped element 26 in communication with a central location of the flattened end profile 28 (such as through a press-fit installation). In this manner, the bulbous seating portion 22 provides rotating ort (see arrow 30) between the annular shaped profile 20 of the secondary receiver 18 and the flattened support profile 28 of the intermediate three dimensional component 26. Without limitation, this can include the surface inter-rotating profile established between surfaces 20 of the secondary receiver 18 and 28 of the intermediate element 26 being established about an axis 27 extending through a center of the bulbous portion 30 and adjoining neck 23, and further such that the rotational interface between the second receiver and intermediate element 26 is perpendicular to the mating surfaces 20/28 of the components.

Separately, a further recess concave profile, largely hidden from view but generally designated at 32 in FIG. 2, is formed in the outward facing perimeter of the scapula mounted first receiver 16 and, in combination with rotating support separately established between the pseudo-spherical intermediate element 26 and the opposite scapula bone mounted receiver 16. This, in combination with the rotational interface established between the second receiver 18 and the intermediate element 26, establishes first rotating and second spaced and articulating surfaces within the joint assembly.

Without limitation, the first receiver 16, second 18 and inter-disposed pseudo-spherical element 26 are each constructed of any suitable material including any type of plastic, metal or admixed composite. While not limited to any specific variant, the material selection for these components can alternate between the components, such as for example the first scapula mounted receiver 16 and second humeral head mounted receiver 18 being constructed of a first material (e.g. heavy duty, wear resistant and sanitary polymeric, polymeric composite, surgical steel/aluminum, other metal or metal composite, as well as plastic/metal admixture), and with the inter-disposed pseudo-spherical element 26 being constructed of a secondary/alternating material selected from such as the other of the identified materials.

Although not shown, the existing arrangement of ligaments, tendons and muscles provide the anchoring/seating support for retaining the articulating relationships established between the first and second uniquely configured receiver shaped elements 16 and 18 and interposed pseudo-spherical element 26, it further being understood that these components are capable of being retrofit installed within the reconditioned bone ends of the patient without the necessity of the ligaments and tendons being severed of otherwise impacted, thereby enhancing the universal motion profile afforded by the design and likewise reducing recovery time for the patient. As previously described, the ability to segment a combination of rotational and universal/articulating motion of the glenohumeral joint into a pair of spaced apart profiles serves to both enhance artificial joint mobility as well as to more evenly distribute an associated wear profile of the joint, thereby increasing expected life of the assembly.

Figure 3:
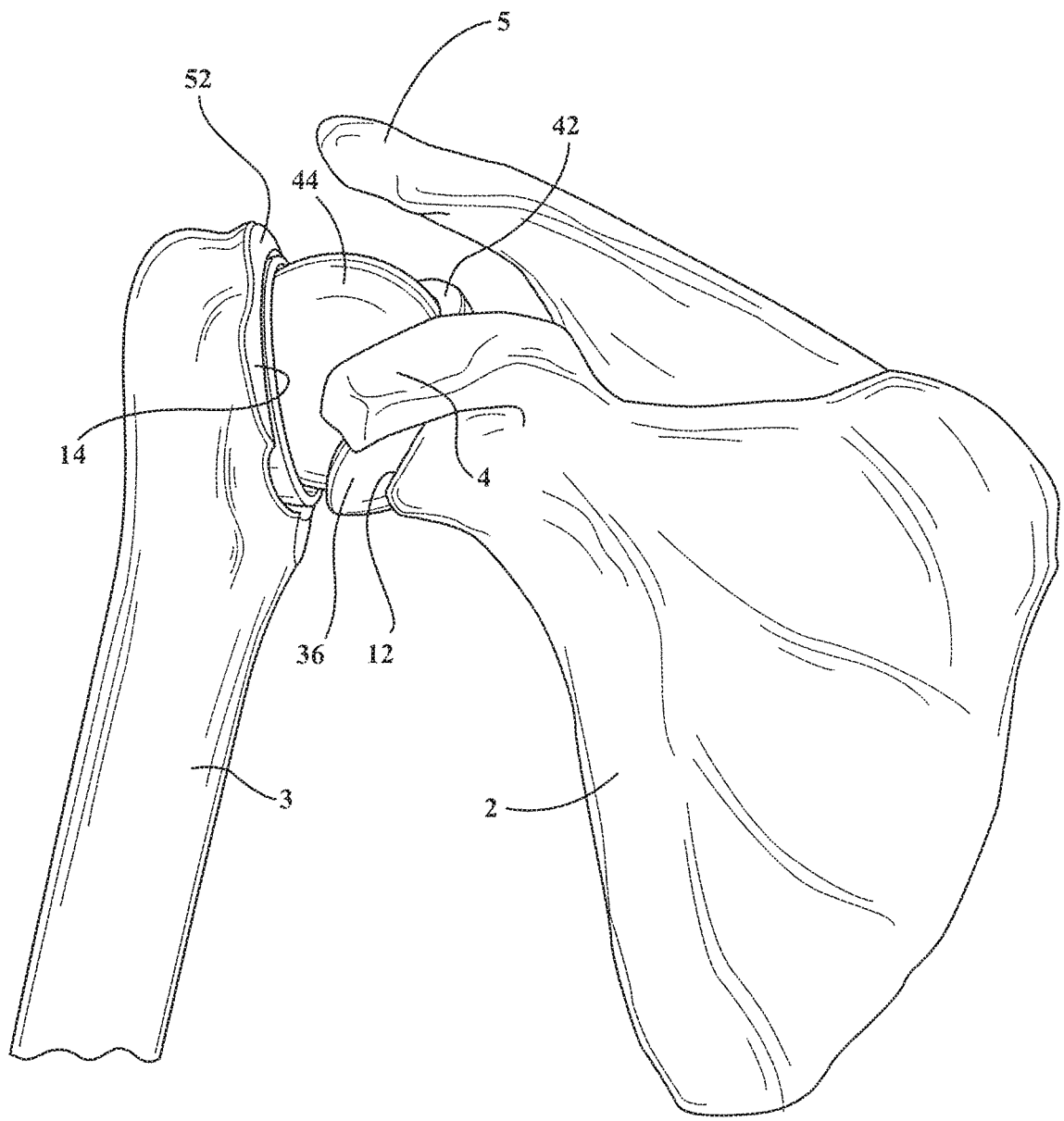
FIG. 3 is an assembled view of a modified shoulder implant assembly of FIG. 2.
Figure 4:
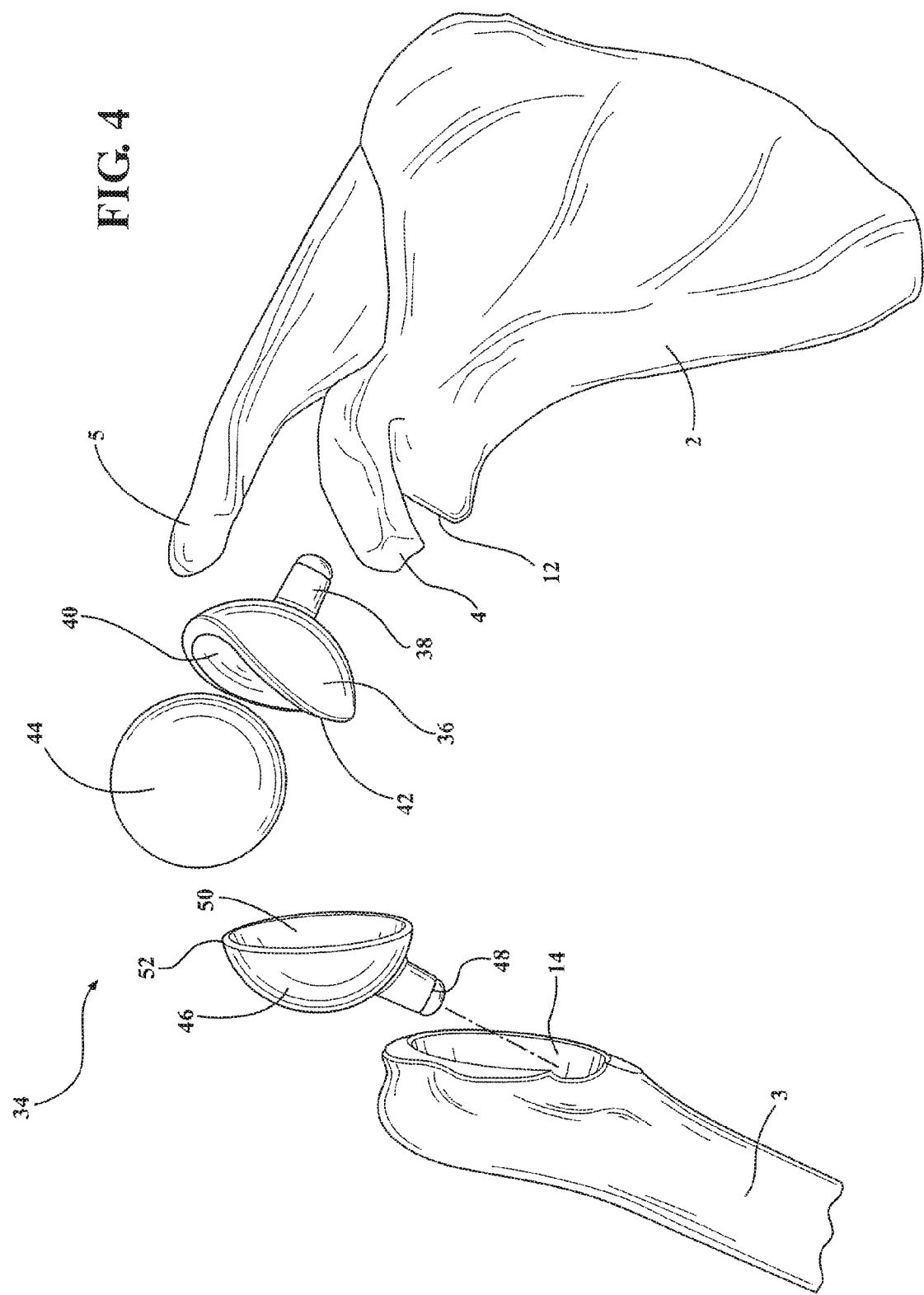
FIG. 4 is an exploded view of the multi-component arrangement of FIG. 3, similar to the previous depiction of FIG. 2, and better illustrating the modified nature of shoulder implant assembly in which a modified/enlarged and tapered concavity profile is formed in the scapula bone mounted receiver component, combined with a redesign of the second humeral head mounted receiver, and with the inter-supported element exhibiting a complete spherical shape.

Referring now to FIGS. 3 and 4, FIG. 4 a pair of assembled and exploded views are shown of a modified shoulder implant assembly, generally at 34, in which a modified/enlarged and tapered concavity profile is formed in the scapula bone mounted receiver component, combined with a redesign of the second humeral head mounted receiver, and with the inter-supported element exhibiting a complete spherical shape. Specifically, redesigned first receiver 36 exhibits an enlarged configuration in comparison to that depicted at 16 in FIGS. 1-2, with similar configured stem mounting portion 38. Enlarged concavity profile 40 is further exhibited and round which extends a tapered perimeter rim 42, such that an intermediate spherical element 44 is seated within the concave profile in the fashion as further depicted in FIG. 3.

A correspondingly redesigned second humeral head mounted receiver 46 exhibits an extending and anchoring stem portion 48 (again generally matching the inner machine profile associated with the humeral head recess 14). A further concave profile 50 is formed in an outwardly facing direction of the second receiver 46 and which is bound by a generally level and planar outer rim 52.

Upon installation, the flared profile 42 of the first scapula mounted receiver 36 provides enhanced universal articulating and shouldering support with one seating side of the spherical intermediate element 44, combined with the additional level of universal articulating and seating support established by the seating profile established by the second receiver element 46. As best shown in FIG. 3, the assembled arrangement is such that the outer tapered profile 42 of the first receiver 36 approaches the outer perimeter rim 52 of the second receiver 46 depending upon the angular orientation established between the humerus bone relative to the scapula, with the overall dimensioning of the seating/support surfaces being such that an optimization of seating support and articulating range of motion is maximized.

With reference to FIGS. 5 and 6, successive assembled and exploded views are respectively shown depicting the arrangement of a scapula mounted first receiver 16, such as depicted in FIGS. 1-2, combined with a second receiver 46 configured as shown in FIGS. 3-4, and in combination again with a fully spherical shaped intermediate component 44 for providing universal articulating support along each of two individual locations established between the humerus mounting receiver 46 and intermediate component 44, and separately an opposite end profile of the intermediate component 44 and the other receiver 16 mounted in the scapula 2. In this fashion, the assembled joint assembly depicted in FIG. 5, differs marginally from that shown in FIG. 3 owing to the less significant degree of shouldering/seating support by the first receiver 16 (in comparison to the enhanced support depicted by the modified receiver 36 of FIG. 4 and which illustrates the tradeoff established between range of motion and support evidenced by these varying implant arrangements) depicted versus that associated with the second humeral head mounted receiver 46.

Figure 10A:
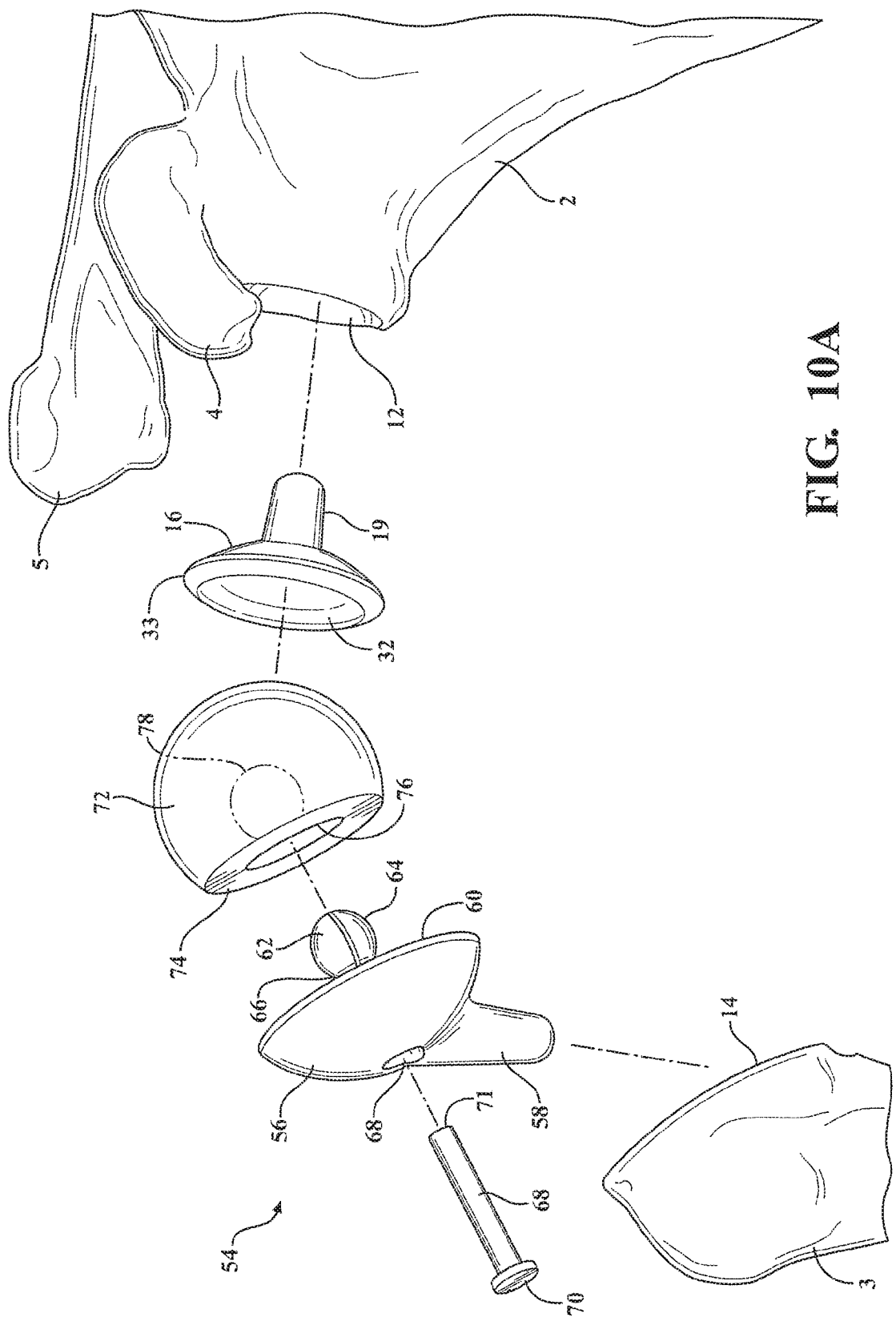
FIGS. 10A and 10B illustrate a variant of the arrangement of FIG. 2 in which a passageway communicates from a rear convex surface of the secondary receiver in extending fashion into the bulbous projection, such that the bulbous portion can exhibit a split or otherwise expandable construction and such that, upon pre-engaging the bulbous projection into the undercut surface communicable portion of the partially spherical shaped element, a pin or other fastener is inserted through the rear surface of the secondary receiver in order to expand the expand the bulbous portion into a more secure engagement with the partially spherical shaped element and while still allowing for inter-rotational support.
Figure 10B:
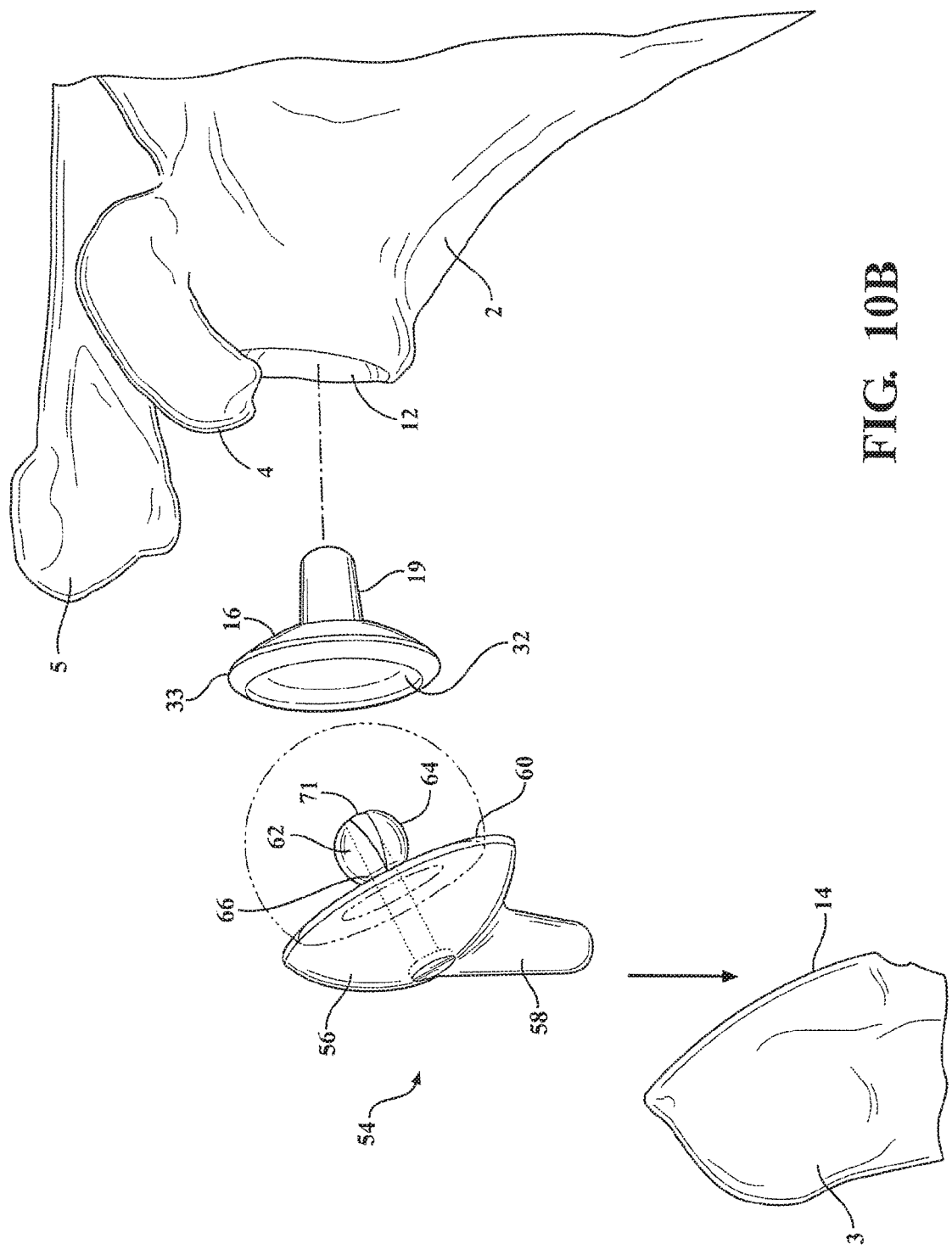

Referring now to FIGS. 10A-10B, a pair of exploded views are generally shown at 54 of a further embodiment of the implant assembly and which illustrate a variant of the arrangement of FIG. 2 in which a reconfigured second receiver 56 is provided with an extending and mounting stem 58, as well as a planar surface profile 60. An expanded portion (also termed a bulbous projection or an arm socket) is exhibited by first 62 and second 64 split portions which project from the planar surface profile 60 via a narrowed neck 66 (see also as shown at 23 in FIG. 2).

A passageway 68 is defined in the second receiver 56 and communicates a rear convex surface with the split portions 62/64. A pin having a shaft 68, an enlarged head 70 at a first end and a second flattened end 71 is provided.

An intermediate positioned pseudo spherical component is again provided and includes a spherical surface portion 72 which is adapted to seat the concave interior 32 associated with the first scapula mounted receiver 16. The first receiver 16 also exhibits a tapered rim 33 extending around an outer perimeter of its concave profile 32 for establishing enhanced shouldering support of the spherical portion 72 of the intermediate component.

The intermediate component also includes a flattened profile 74 in communication with the spherical portion 72, an enlarged passageway defining aperture (see inner perimeter wall 76) being defined within the flattened profile 74 and extending within the interior of the intermediate component in a similar fashion compared to that shown at 25 in FIG. 2. Upon pre-seating the split portions 62/64 through the narrowed entranceway 76 communicating with the undercut profile (see further in phantom at 78) and extending inwardly from the flattened surface profile 74, the pin is inserted through the passageway 68 from the rear surface of the secondary receiver 56 and, upon being fully installed as shown in FIG. 10B, its flattened end 71 engages between the split portions 62/64, such that they are expanded outwardly into engagement with the undercut profile 78. In this fashion, the intermediate component establishes the inter-rotational interface with the second humeral head mounted component 56 while concurrently providing an articulating interface with the first scapula mounted component 16.

Figure 11A:
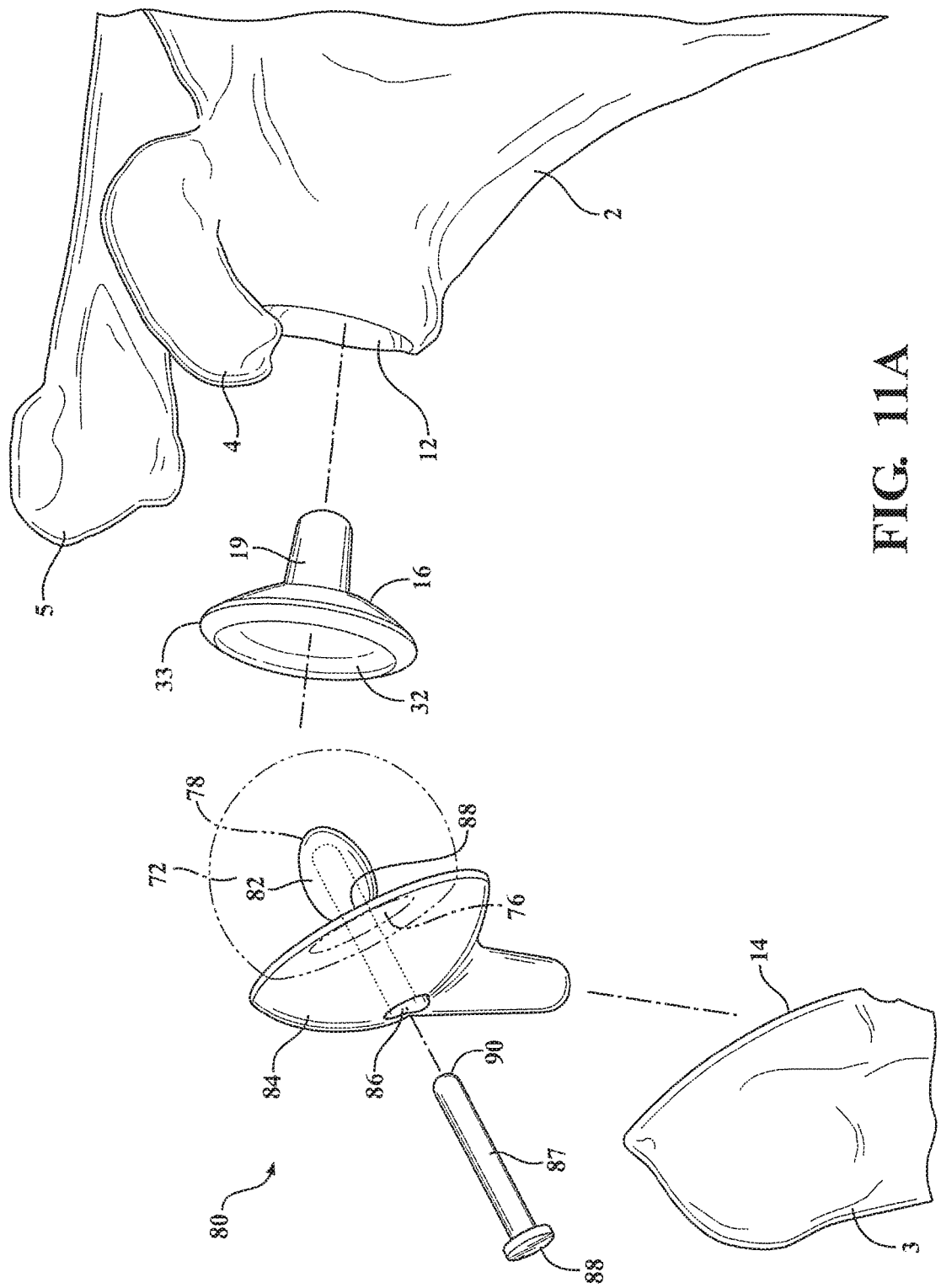

Proceeding to FIGS. 11A and 11B, a pair of illustrations are provided of another variant of the implant assembly, generally at 80, which is similar in most respects to that depicted FIGS. 10A-10B, the exception being the provision of a reconfigured bulbous portion 82 projecting from a planar surface associated with a similarly constructed second receiver 84. The bulbous projection 82 can be constructed of an expandable material and which may further be reconfigured without a split profile.

As is further understood, the second receiver 84 (as well as the first receiver 16 and/or the intermediate pseudo-spherical component) can be constructed of a plastic or metal. This can occur such as in an alternating material construction between the three components so as to minimize wear and optimize its useful life. In the instance of the second receiver 84, the bulbous portion can constitute a softer and expandable thermoformed plastic or synthetic rubber, and which is co-injection molded with a harder plastic or like composite.

As with the variant of FIGS. 10A-10B, a passageway 86 extends from a rear surface of the second receiver 84 and receives a similarly constructed pin 87 having a first enlarged rear head 88 and a forward/arcuate contoured end 90. The passageway 86 extends to an interior location of the bulbous portion 82 (see in phantom in FIG. 11A).

The bulbous portion 82 (also termed an arm socket) in FIG. 11A further exhibits a pseudo-elliptical and extended shape and the interior of the passageway 86 may be partially or substantially filled with a compressible material such as a packaged gel or other flowable fill material (see at 88). In this fashion, and upon pre-seating the bulbous projection or arm socket into the undercut defined interior of the intermediate component, the pin 87 is inserted through the passageway 86 associated with the second receiver 84 (in similar fashion as previously described in reference to FIG. 10B). At this point, the forward end 90 of the pin compresses the fill material 88, with the result being that the initially elliptical shape of the arm socket/bulbous projection 82 (FIG. 10A) is reconfigured into a width expanded shape 82' (FIG. 11B) and so that the bulbous projection is expanded into the undercut/width expanded interior 78 in a manner which establishes an inter-rotational interface between the intermediate component and the second humeral head mounted receiver, this concurrent with the articulating support profile established between the spherical surface portion 72 of the intermediate component and the first scapula mounted receiver 16.

Figure 12:
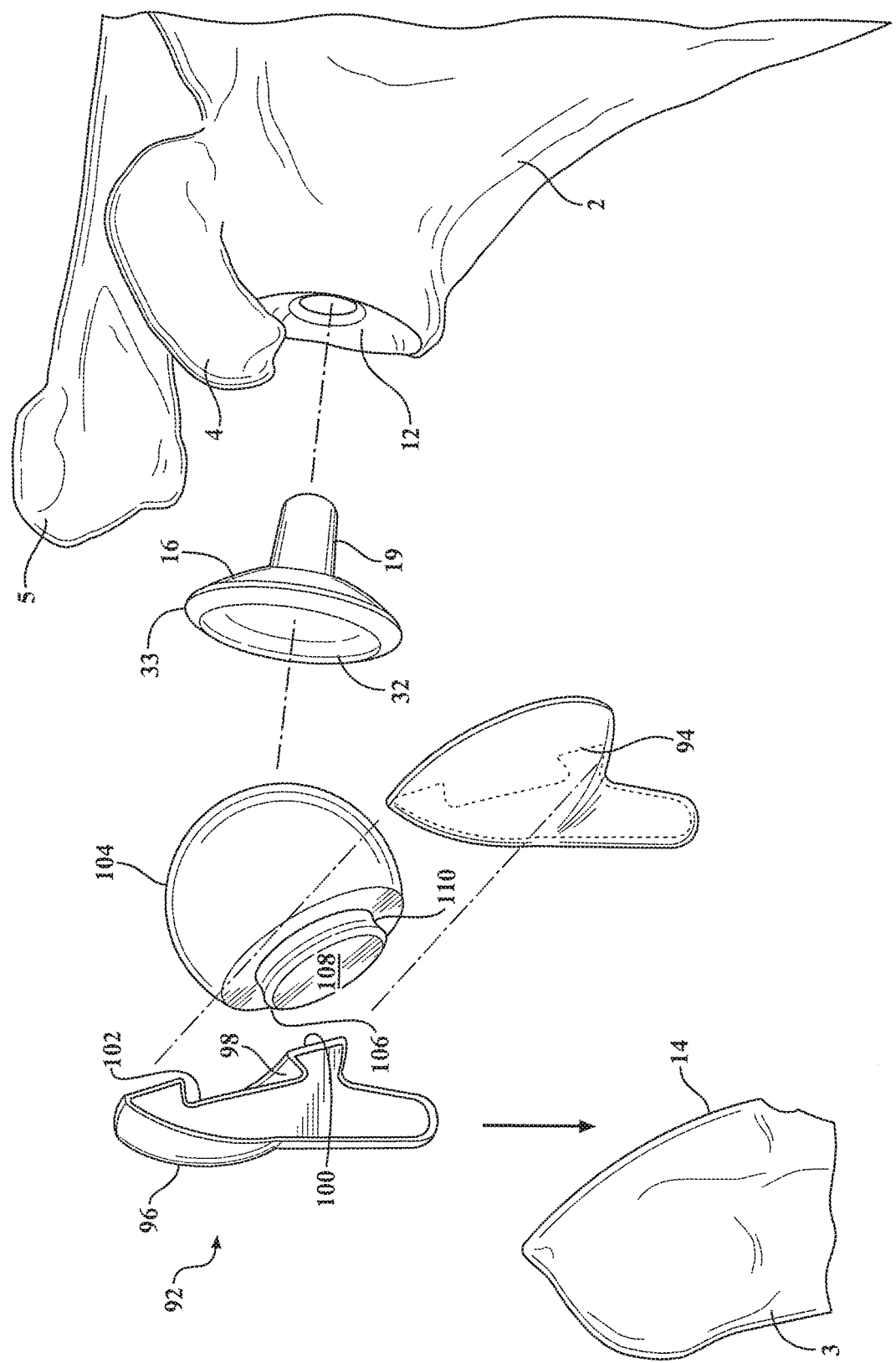
FIG. 12 is an exploded illustration of a further embodiment in which the second receiver is reconfigured as first and second linearly split halves with each of the halves exhibiting an interior extending and undercut profile in communication with its flattened end profile, upon assembly of the halves, the undercut profile being configured to capture therebetween a mating portion associated with a reconfiguration of the pseudo-spherical and intermediate component and which projecting from its flattened end profile.

FIG. 12 is an exploded illustration of a further embodiment, generally at 92, in which the second receiver is reconfigured as first 94 and second 96 linearly split halves. Each of the halves 94 and 96 exhibit an interior extending and undercut profile, see as defined by undercut profile visible in second halve 96 and including an outer semi-circular and undercut side surface 98 extending inwardly from a flattened exterior profile 100, the undercut side surface 98 terminating in a recessed interior base surface 102 in communication with the flattened end profile 100.

A reconfiguration of the pseudo-spherical intermediate component includes a spherical portion 104 communicating in a planar end surface 106. A further mating portion 108 projects from the planar end surface 106 and, upon assembly of the second receiver split halves 94 and 96 (such as which can further include any of tab and slot, finger and decent, or other inter-engaging features established along opposing perimeter edges of the halves 94 and 96 for snapping them together), the undercut profile defined between the receiver halves 94/96 is configured to capture therebetween the mating portion 108 associated with a reconfiguration of the pseudo-spherical and intermediate component.

In this fashion, the exterior surface 100 of the assembled second receiver supports the outer annular extending profile of the planar surface 106 of the intermediate component (see spherical portion 104), with the end face of the projecting mating portion 108 (with outwardly annular side wall 110) is captured within the undercut recess (side 98 and recessed interior 102) established by the assembled halves. As further previously described, the first receiver 16 and second assembled receiver 94/96 are glued or otherwise affixed to the reconditioned mounting surfaces (sockets) established within the scapula 2 and humeral head 3 (the gluing or other affixation of the assembled second receiver occurring following assembly about the projecting mating portion 108 of the intermediate component) and to collectively define a first articulating interface established between the spherical portion 104 of the intermediate component and the first scapula mounted receiver 16, concurrent with establishing a second rotating interface between the projecting portion 108 of the intermediate component and the undercut support defined in the assembled second receiver halves 94/96.

Figure 13:
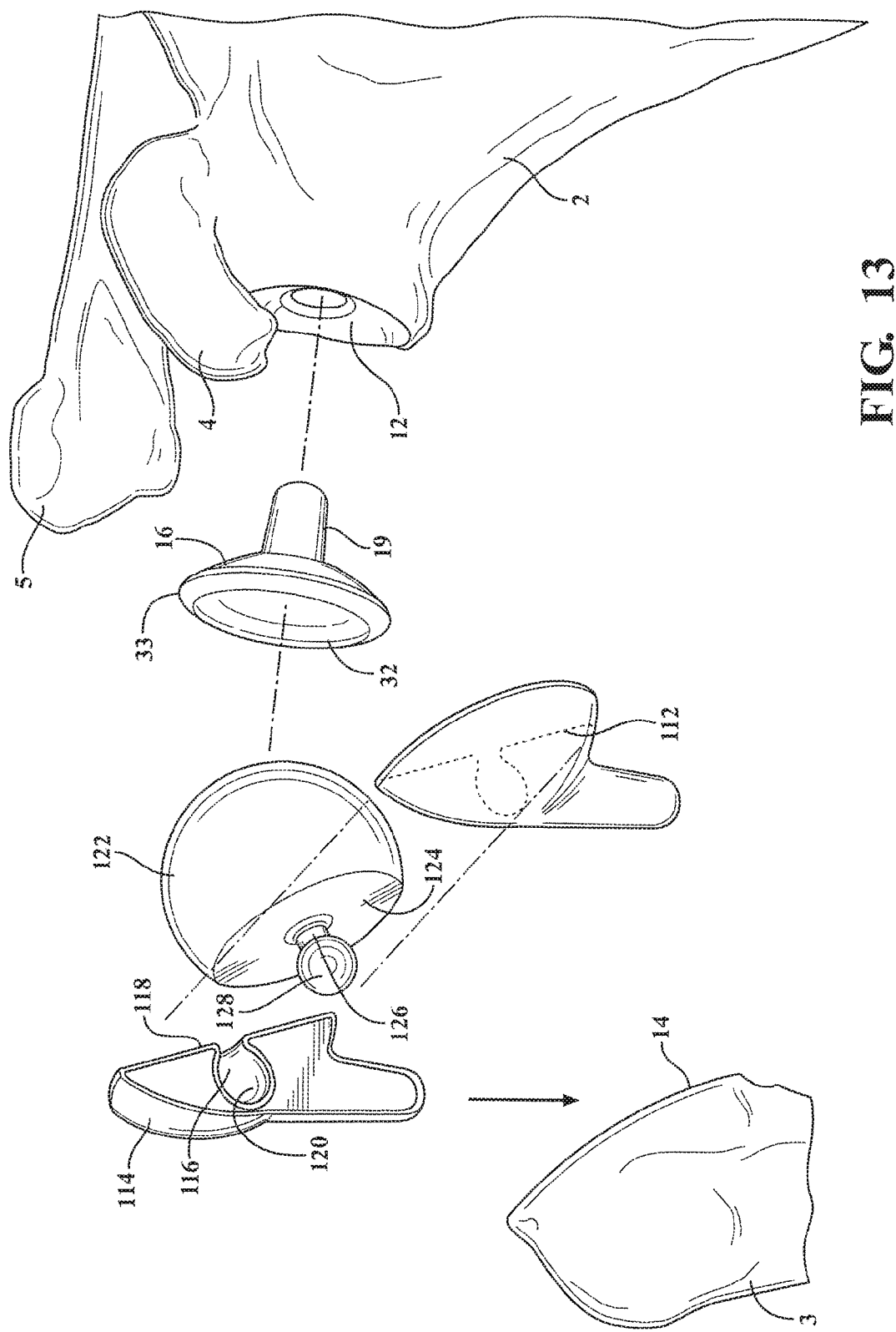
FIG. 13 is an illustration similar to FIG. 12 and depicting an alternately configured pair of split halves associated with the second receiver, these exhibiting a different interior expanding profile for pre-assembling in capturing fashion a bulbous projection of the intermediate component extending from its flattened end profile.

Finally, FIG. 13 is an illustration similar to FIG. 12 and depicting an alternately configured pair of split halves 112/114 associated with the second receiver, these exhibiting a different interior expanding profile (see for selected halve 114 and including narrowed entranceway 116 extending inwardly from exterior surface 118 and communicating with arcuate expanded interior profile 120) as compared to that shown in FIG. 12. The intermediate (pseudo-spherical) component is likewise reconfigured to include a spherical portion 122 communicating with a flattened end profile 124, a bulbous arm socket portion having a narrowed neck or stem 126 extending from a central location of the flattened end profile 124 and communicating with a widened bulbous end portion 128.

In similar fashion as described in FIG. 12, and upon pre-assembling the split halves 112 and 114 together (such as again using any inter-engaging configuration established between the halves captures the bulbous projection 128 within the undercut/expanded profile 120) the second receiver is then mounted within the humeral head. As with the description of FIG. 11, and upon completed in situ implantation, the intermediate component is both supported in an articulating interface relative to the first receiver 16 as well as in a rotating interface with the second assembled receiver, halves 112/114.

Having now described our invention, other and additional preferred embodiments will become evident to those skilled in the art to which it pertains, and without deviating from the scope of the appended claims.

I claim:

1. An implant assembly for re-establishing a glenohumeral joint between a scapula and humerus, comprising:
   a first receiver adapted to being mounted to a reconditioned glenoid cavity defined in the scapula, said first receiver exhibiting a concave profile;
   a second receiver adapted to being mounted to a reconditioned humeral head associated with the humerus, said second receiver further including first and second linearly split and mating halves, said split halves having mating edges exhibiting aligning interior extending undercut profiles, a flattened perimeter surface surrounding the undercut profiles;
   an intermediate component interposed between said first and second receivers such that a spherical portion of said intermediate component seats against said concave profile of said first receiver in a first universally articulating interface with said first receiver; and
   said intermediate component further having a flattened end surface in edge communication with said spherical portion, a width expanding portion projecting from a central location of said flattened end surface and which, upon pre-assembling of said mating halves, captures said expanding portion within said interior undercut profile so as to limit said intermediate component to rotate relative to said second receiver and so that said flattened end surface of said intermediate component abuts with and rotates relative to said flattened perimeter surface of said assembled second receiver to establish a second rotational interface between said intermediate component and said second receiver.

2. The implant assembly as described in claim 1, said undercut profiles of said second receiver split halves each further comprising a narrowed entranceway extending inwardly from said flattened perimeter surface and communicating with an expanded semi-spherical interior profile, said width expanding portion of said intermediate component further having a spherical profile extending from a narrowed stem which is captured between a spherical assembled interior profile defined between said split halves.

3. The assembly as described in claim 1, each of said first and second receiver components and interposed spherical component being constructed of an alternating material including at least one of a polymer, polymer composite, metal, metal composite or polymer/metal admixture.

4. The assembly as described in claim 1, further comprising a snap fit engagement established between said mating edges of said split halves.

* * * * *